United States Patent
Barbuzzi et al.

(10) Patent No.: US 6,689,347 B2
(45) Date of Patent: Feb. 10, 2004

(54) HAIR CARE COMPOSITIONS

(75) Inventors: Elena Maria Gabriella Barbuzzi, Merseyside (GB); Wolfgang Robert Bergmann, Chicago, IL (US); Mrunalini Dhamdhere, Chicago, IL (US); Kevin Ronald Franklin, Merseyside (GB); Cheryl Anne Taylor, Merseyside (GB); Nicola Whilton, Merseyside (GB)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 0 days.

(21) Appl. No.: 10/135,996

(22) Filed: Apr. 30, 2002

(65) Prior Publication Data

US 2003/0064047 A1 Apr. 3, 2003

(30) Foreign Application Priority Data

Apr. 30, 2001 (EP) .......................................... 01303914
Feb. 19, 2002 (EP) .......................................... 02251123

(51) Int. Cl.$^7$ ............................................... A61K 7/075
(52) U.S. Cl. ................. 424/70.12; 424/70.1; 424/70.11
(58) Field of Search ............................ 424/70.1, 70.11, 424/70.12

(56) References Cited

FOREIGN PATENT DOCUMENTS

| EP | 0846662 A2 | 6/1998 |
| EP | 1038834 A1 | 9/2000 |
| JP | 10/114622 | 5/1998 |
| WO | 01/30310 | 5/2001 |

*Primary Examiner*—Jyothsna Venkat
(74) *Attorney, Agent, or Firm*—Milton L. Honig

(57) ABSTRACT

This invention relates to an aqueous hair care composition comprising water-insoluble particles having a layered structure comprising oxygen atoms and silicon and/or phosphorus atoms, and comprising organic functional groups which are bonded to silicon and/or phosphorus atoms in the layers by covalent bonds.

7 Claims, No Drawings

HAIR CARE COMPOSITIONS

TECHNICAL FIELD

This invention relates to hair care compositions and to their use in the care of hair.

BACKGROUND AND PRIOR ART

Shampoo compositions are generally formulated with highly effective cleansing surfactants, typically anionic surfactants, and do not in themselves provide much conditioning or styling benefit to the hair. In fact, basic shampoo formulations which have not been supplemented with specific conditioning or styling agents have a tendency to leave the hair in a cosmetically-unsatisfactory condition with regards to manageability and stylability. The hair tends to have a harsh, dull and dry feel, often referred to as "creak", is often difficult to comb, in either the wet or the dry state, typically has poor brushing properties, and tends to have poor set-retaining abilities.

This has resulted in the use of products containing specific conditioning and/or styling agents. Such agents are generally applied separately after shampooing and rinsing the hair, for example, in the form of conditioner formulations or styling mousses etc. Alternatively, conditioning and/or styling agents have been incorporated into the shampoo formulations. Although the latter approach provides the advantage of removing the need for a separate conditioner or styling treatment, the conditioning and/or styling agents are not always compatible with the shampoo ingredients, especially the anionic surfactant. This can result in the cleansing action and/or cosmetic benefit being compromised.

One of the most common methods for imparting styling benefits to the hair has been the use of hair fixative agents, such as high molecular weight polymers. The problem with using such agents is that they have a tendency to negatively impact on conditioning attributes such as wet and dry stage clean feel and smoothness. In fact, they can result in a sticky feel to the hair.

Conventional styling polymers are typically water-soluble. This means that when incorporated into a shampoo or conditioner which is rinsed off the hair, there is a tendency for the styling polymer to be washed away to a greater or lesser degree with the shampoo/conditioner. Hence, most styling products are leave-in products, which are applied to the hair as post-shampoo/conditioner treatments.

The problem being addressed by the present invention is the provision of hair care compositions, in particular rinse off compositions which impart styling benefits, and in particular body benefits on the hair, but which do not compromise the cleansing action of the shampoo and which do not negatively impact on the conditioning attributes of the hair. The body benefits or attributes the present invention is looking particularly to provide are root lift, increased hair volume, bounce, control (i.e. ease of styling) and manageability, i.e. maintenance of style without undue stiffness and negative sensory feel. Such body attributes are particularly attractive to people with fine or long, weighty hair.

One way in which this problem has been addressed in the past has been to include conditioning agents, for example silicones and cationic surfactants, in the compositions, to counter the negative effects of the styling agents. Although such conditioning agents do provide substantial improvements in for example the wet and dry combing properties of the hair and in the smoothness of the hair, they tend to have a negative effect on many of the attributes associated with hair body.

We have now found that the inclusion of a certain level of functionalised clay material in hair care formulations provides substantial styling benefits, in particular with regards to imparting body attributes to the hair. Furthermore, the conditioning attributes of the hair are not adversely affected by the use of hair compositions containing these particles and there is no necessity to incorporate additional conditioning agents or specialised surfactant systems. The compositions of the present invention are also stable.

The use of clays in hair care compositions is known. Clays have been used for example as structurants and as grease absorbers. However, the use of functionalised clays in hair care compositions has not previously been disclosed.

The incorporation of the functionalised clay material into the hair care compositions of this invention leads to substantive improvements in the body of the washed and optionally conditioned hair, especially if a subsequent styling regime is followed. The compositions impart body attributes, such as are root lift, volume, bounce and manageability, in the absence (or substantial absence) of a styling polymer, which leads to compositions which have a styling benefit, but nevertheless do not suffer from the sensory negatives (e.g. stickiness and/or dry feel) which are associated with prior styling compositions which are based on, for example, a styling polymer.

DEFINITION OF THE INVENTION

Accordingly, this invention provides an aqueous hair care composition comprising water-insoluble particles having a layered structure comprising oxygen atoms and silicon and/or phosphorus atoms, and further comprising organic functional groups which are covalently bonded to the silicon and/or phosphorus atoms in the layers.

Additionally, this invention provides for the use of water-insoluble particles as defined above in a hair care composition to impart body.

A method of treating hair is also disclosed which comprises the following steps:

i) wetting the hair;
ii) applying the product according to the invention;
iii) rinsing the hair

DETAILED DESCRIPTION AND PREFERRED EMBODIMENTS

Definitions

Unless specified otherwise, all wt % values quoted hereinafter are percentages by weight based on total weight of the hair care composition.

$D_{3,2}$ average droplet or particle sizes as referred to herein may be measured by means of a laser light scattering technique, using a 2600D Particle Sizer from Malvern Instruments.

In this specification organic functional groups are interpreted as any group including a carbon atom, in particular compounds in which the linking group from the clay is to a carbon atom or a silicone atom.

The term "hair care composition" is intended to mean compositions for shampooing, conditioning and styling hair.

The present invention is based on the application in the treatment of hair of water insoluble particles having a layered structure comprising oxygen atoms and silicon and/or phosphorus atoms, and comprising organic functional groups which are bonded to silicon and/or phosphorus atoms in the layers by direct covalent bonds to carbon i.e., covalent bonds between silicon and carbon (Si—C bonds) or between phosphorus and carbon (P—C bonds). It is preferable if the linkage from the organic group to the clay is through a Si—O—C bond or a Si—O—Si bond. The oxygen can originally be part of the organic group or part of the clay.

Water-insoluble Particles

The present invention involves the use of water-insoluble particles having a layered structure comprising oxygen atoms and silicon and/or phosphorus atoms, and comprising organic functional groups which are bonded to silicon and/or phosphorus atoms in the layers. The term "water-insoluble", as used herein, means that the particles are soluble in distilled water at a concentration of less than 0.01 g/l, preferably less than 0.001 g/l at 20° C. Preferably, the particles will be substantially insoluble but dispersible in water at 20° C.

The water insoluble particles used in the invention are of a size such that they are not perceived as distinct particles to the touch. Preferably, the particles used in the invention have an average size of from 0.1 to 100 $\mu$m. More preferably, the particles used herein have an average size in the range of from about 1 $\mu$m to 50 $\mu$m. The size of the particles refers to their maximum dimension, such as their diameter when the particles are substantially spherical.

The layered nature of the particles preferably involves an ordered array comprising oxygen atoms and silicon and/or phosphorus atoms. The layers may also comprise other metallic and/or non-metallic atoms. Other atoms which may be present in the layers include, for example, di- and/or trivalent metal atoms, such as of alkaline earth metals (e.g., magnesium or calcium), of transition metals (e.g., copper, nickel and/or zirconium), of Group IIIB of the periodic table (e.g., aluminium) or of mixtures thereof. Suitable particles may comprise discrete, repeating units of layers or sheets. Layers or sheets are substantially two-dimensional arrays of atoms. Preferably, the repeating unit consists of a plurality of (e.g., two or three) layers, or sheets, of atoms with a metallic atom or a mixture of metallic atoms forming the central layer and a range of non-metallic atoms bridging and/or forming the surrounding layers. Also present within the repeating unit may be a variety of atomic, ionic or molecular species, including for example, polyvalent metal ions such as sodium and/or calcium and/or hydroxonium ions.

Suitable examples of layered structures include those comprising divalent or trivalent metal ions, or a mixture thereof, in the central layer. Preferably, the central layer comprises magnesium, nickel, ziconium or aluminium ions, or mixtures thereof, which are connected via oxygen atoms and/or hydroxyl groups to the surrounding layer. Preferably, the surrounding layers comprise a mixture of silicon atoms and oxygen atoms as well as other cationic and/or molecular species.

The interlayer spacing in the particles which are used in the invention is preferably greater than 10 Å, more preferably greater than 12 Å, as determined by X-ray crystallography. The interlayer spacing preferably does not exceed about 100 Å and, more preferably, it does not exceed about 50 Å.

When the central layer comprises divalent ions and the outer layer comprises silicon atoms, with bridging oxygen atoms and hydroxyl groups, the layered structure is analogous to that of talc-like smectite, or phyllosilicate clays.

Smectite clays can broadly be differentiated on the basis of the number of octahedral metal-oxygen arrangements in the central layer for a given number of silicon-oxygen atoms in the outer layer. Those clays featuring primarily divalent metal ions comprise the prototype talc and the members hectorite, saponite, sauconite and vermiculite. When the clays feature primarily trivalent metal ions the structures change and now comprise the prototype pyrophillite, montmorillonite, nontronite and volchonskoite.

Particularly suitable clays have been subject to a de-lamination process before they are added to the composition. It is preferable if the de-lamination process reduces the clay to 10 layers or less, more preferably 5 layers of less, most preferably from 2 to 4 layers.

It is preferable if the smallest dimension of the water insoluble particle is no more than 10% of the biggest dimension of the particle.

The water insoluble particles comprise one or more organic functional groups. The functional groups in each particle may be a single type of functional group or a mixture of different types of functional groups. These organic functional groups can be at least partly responsible for conferring the desired properties on the hair, after treatment with the particles or compositions comprising the particles.

The organic functional groups comprise at least one carbon atom and are bound by a covalent bond to the silicon or phosphorus atom, which forms part of a layer in the water-insoluble particles. Preferred organic functional groups include alkyl, alkenyl, alkynyl, aralkyl and aryl groups, optionally substituted. Optional substituents include, for example, one or more of the same or different groups selected from halo, OR', OCOR$^1$, NR$^2$R$^3$, N$^+$R$^4$R$^5$R$^6$, COX, NCO, NO$_2$, SO$_2$R$^7$, SO$_3$H, H$_2$PO$_4$, PO(OR')$_2$ and heterocycloalkyl, wherein X is selected from halo, OR$^8$, OCOR$^9$, OH, H and R$^{10}$ and R', R$^1$, R$^2$, R$^3$, R$^4$, R$^5$, R$^6$, R$^7$, R$^8$, R$^9$ and R$^{10}$ are independently selected from C$_1$ to C$_6$ alkyl, C$_2$ to C$_6$ alkenyl and hydrogen. When the organic functional groups comprise acid groups, such as CO$_2$H, SO$_3$H, OH or H$_2$PO$_4$, they may be in the form of the corresponding deprotonated ions (e.g., as sodium salts). Especially preferred is the quaternary ammonium group, particularly a C$_1$–C$_5$ quaternary ammonium group.

The term "halo" means fluoro, chloro, bromo or iodo. Suitable halo-substituted groups include, for example, fluoroalkyl, such as perfluoroalkyl.

The term "alkyl" includes C$_1$ to C$_{20}$ (preferably C$_1$ to C$_{12}$, more preferably C$_1$–C$_6$) branched or unbranched acyclic groups and, for C$_3$ to C$_8$, cyclic groups. Acyclic alkyl groups may be substituted in the chain by one or more S or O atoms or NH groups and/or substituted on the chain by one or more =O groups. Optionally substituted acyclic alkyl groups include, for example, optionally substituted methyl, ethyl, n-propyl, iso-propyl, n-butyl, iso-butyl, tert-butyl, n-pentyl and n-hexyl. Optionally substituted cycloalkyl groups include, for example, optionally substituted cyclopropyl, cyclobutyl, cyclopentyl and cyclohexyl. Cycloalkyl groups may be substituted in the ring by one or more S or O atoms or NH groups and/or substituted on the ring by one or more =O groups.

The terms "alkenyl" and "alkynyl" are defined similarly to the term "alkyl" but include, respectively, one or more carbon-carbon double bonds or carbon-carbon triple bonds.

The term "aryl" includes aromatic, heterocyclic and carbocyclic ring compounds, which may be single rings or fused rings. Heterocyclic aryl groups include, for example, pyridyl, pyrrolyl, thiophenyl and furanyl. Carbocyclic aryl groups include phenyl and naphthyl.

The term "aralkyl" means alkyl substituted with aryl e.g., benzyl.

The term "heterocycloalkyl" includes $C_3$ to $C_8$ (preferably $C_3$ to $C_6$) cyclic groups containing one or more heteroatoms in the ring. Heteroatoms include one or more of the same or different groups or atoms selected from O, S, NH and N-alkyl. Heterocyclic alkyl groups may be substituted in the ring with, for example, one or more keto (C=O) groups. Heterocycloalkyl groups therefore include, for example, epoxide, aziridine, azetidinium, lactones, azalactones and cyclic anhydrides (e.g., succinic anhydride) and mono- and di-saccharides (e.g., a group derived from glucose, fructose or sucrose). Polysaccharides (including, for example, dextrins, dextrans, cellulose and modified cellulose) are also suitable functional groups for use in the invention.

It has been found that, in a preferred embodiment of the invention, the use of hair compositions comprising water-insoluble particles having a layered structure and comprising one or more organic functional groups which are capable of self cross-linking and/or reacting with the fibres of the hair leads to improved styling benefits, i.e., improved body attributes, without the negative disadvantages associated with the use of conventional styling agents.

In a preferred embodiment of the invention, the organic functional group is capable of self cross-linking and/or of forming covalent bonds with the surface of a hair fibre e.g. proteinaceous fibres. Proteins possess a range of functional groups. Preferably, the organic functional groups comprise electrophilic groups, which are capable of reacting with hydroxyl groups in proteinaceous fibres and/or thiol groups for more specific reaction with the proteinaceous fibres. Suitable examples of electrophilic groups include: acid anhydrides, epoxides, amines, acid chlorides, isocyanates, azetidinium-containing groups, carboxylic acids, vinyl sulfones, sulphoxy groups, thiols, aldehydes, ketones, enol esters, aziridines, azalactones and mixtures thereof.

It is especially preferred the organic functional group is silane or siloxane, more particularly a silane having the

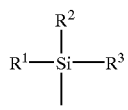

general formula
in which $R^1$, $R^2$ and $R^3$ are independently selected from a $C_1$ to $C_4$ alkyl chain or a $C_2$ to $C_4$ alkenyl chain.

In hair treated according to the invention, with these compositions of the invention, the water-insoluble particles may be cross-linked to each other and/or bound to the surface of hair fibres. Preferably, the water insoluble particles are cross-linked to each other and bound to the fibres.

The water insoluble particles are preferably of a clay functionalised by the introduction of organic functional groups during its synthesis. The organic functional groups may be converted to different organic functional groups by reaction of the clay, after it has been synthesised, with an appropriate reagent, to form another clay, which is suitable for use in the present invention. Appropriate reagents and reaction conditions for the interconversion of functional groups are well-known to those skilled in the art. Alternatively, the clay may need no conversion of functional groups prior to use in the compositions of the invention.

More preferably, the water insoluble functionalised particles are of the general class of inorganic-organic hybrid clays known as an organo(phyllosilicates). Examples of synthetic methods for forming organo(phyllosilicates), or organoclays, are described in *J. Mater. Chem.*, vol. 8, 1998, p 1927–1932, *J. Phys. Chem. B.* 1997, 101, 531–539, *J. Chem. Soc., Chem. Commun.*, 1995, 241–242 and *J. Mater. Chem.* 2000, 10, 1457–1463. In these examples, the organic functionality is introduced into the clay by assembling a metal oxide/hydroxide framework in the presence of an organotrialkoxysilane. The water insoluble particles of the present invention are preferably produced according to this method. Therefore, the water-insoluble particles are preferably obtainable by the hydrolysis of an organotrialkoxysilane in the presence of at least one di- or tri-valent metal ion in an alcoholic solution at a suitable pH appropriate to the metal ion used. The skilled person is readily able to determine a suitable pH for the hydrolysis on the basis of the teaching of the prior art. For example, for magnesium, the pH is typically greater than 7 and for aluminium it will typically be in the range of from pH 5–12 (preferably from 5.5 to 6.5).

Other water insoluble functionalised particles are also suitable for use in the present invention. For example, metal organophosphates (including zirconium (which is preferred), titanium, hafnium, vanadium (V), magnesium (II), manganese (II), calcium (II), cadmium (II), lanthanum (III), samarium (III), cerium (III) and iron (III)) can be prepared by a precipitation reaction involving mixing a solution of the metal ion and a solution of an organic phosphoric or phosphinic acid. Crystallisation of the layered structure results. Synthetic routes of this type are described, for example, in *Acc. Chem. Res.*, 1992, 25, 420–427, *Chem. Mater.* 1994, 6, 2227, *Acc. Chem. Res.*, 1978, 11, 163 and *Chem. Rev.*, 1988, 88, 55. Zirconium organophosphates, and other metal organophosphates, typically comprise, in each layer, a plane of metal atoms linked together by phosphonate groups. The metal atoms are preferably octahedrally coordinated by oxygen atoms, with the three oxygen atoms of each phosphonate tetrahedron bound to three different metal atoms.

The preferred water-insoluble particles used in the invention are organoclays and more preferably three-layer clays consisting of a central metal-containing layer, as in the analogous talc-like structures, together with bridging oxygen and hydroxyl groups and silicon atoms in the outer two layers. Unlike talc, however, the outer silicon atoms are attached to organic groups as well as oxygen atoms.

Preferably, a high proportion (for example greater than 50% by number, more preferably greater than 75% by number) of the Si atoms in any given organoclay particle are covalently bonded to at least one carbon atom. However, the layered structure may contain varying amounts of Si atoms that are not covalently bonded to a carbon atom, and these particles will also operate effectively within the scope of the invention.

The organoclays preferably comprise silicon or phosphorus, oxygen, metal (e.g., magnesium, nickel, zirconium or aluminium or mixtures thereof), in addition to the organic functional groups and the organic functional groups in the water insoluble particles.

Preferred particles of the invention may have the general formula

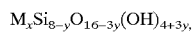

wherein:
M is Mg, Ni, Cu or Al
x is 6 when M is Mg, Ni or Cu; and 4 when M is Al
y is between 0 and 4

In a particularly preferred example of the invention, the organoclay may be represented by the formula $Mg_6Si_8R_8O_{16}(OH)_4$, with a silicon to magnesium ratio of 1.13 and where R is any one of the suitable organic functional groups listed above. R may, for example, comprise a reactive functional group, as described hereinbefore, and a divalent linker group such as a $C_1$ to $C_{18}$ (preferably $C_1$ to $C_{12}$) branched or unbranched alkylene group e.g., $(CH_2)_n$ where n is an integer from 1 to 6. The linker group is bound at one end to the organic functional group capable of reacting with a cellulosic or proteinaceous fibre and at the other end to a silicon atom.

A particularly preferred clay for use with the present invention is trimethyl siloxyl bentonite.

Treatment of hair with the hair care compositions of the invention comprises any step in which the compositions are applied to hair.

Typically, application occurs with the composition in the form of an aqueous dispersion or suspension. Treatments include washing and conditioning of the hair.

The water insoluble particles having a layered structure and comprising one or more organic functional groups are preferably present in the hair care composition in an amount of from 0.01 to 10 wt %, more preferably from 0.1 to 5 wt % and most preferably 0.1 to 3 wt % of the total composition.

Hair Care Compositions

Compositions in accordance with the invention are formulated as compositions for the treatment of hair and subsequent rinsing.

Shampoo Compositions

A particularly preferred hair care composition in accordance with the invention is a shampoo composition.

Such a shampoo composition will comprise one or more cleansing surfactants which are cosmetically acceptable and suitable for topical application to the hair. Further surfactants may be present as an additional ingredient if sufficient for cleansing purposes is not provided as emulsifier for the silicone component. It is preferred that shampoo compositions of the invention comprise at least one further surfactant (in addition to that used as emulsifying agent for the silicone component) to provide a cleansing benefit.

Suitable cleansing surfactants, which may be used singularly or in combination, are selected from anionic, amphoteric and zwitterionic surfactants, and mixtures thereof. The cleansing surfactant may be the same surfactant as the emulsifier, or may be different.

Anionic Cleansing Surfactant

Shampoo compositions according to the invention will typically comprise one or more anionic cleansing surfactants which are cosmetically acceptable and suitable for topical application to the hair.

Examples of suitable anionic cleansing surfactants are the alkyl sulphates, alkyl ether sulphates, alkaryl sulphonates, alkanoyl isethionates, alkyl succinates, alkyl sulphosuccinates, N-alkyl sarcosinates, alkyl phosphates, alkyl ether phosphates, alkyl ether carboxylates, and alpha-olefin sulphonates, especially their sodium, magnesium, ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from 1 to 10 ethylene oxide or propylene oxide units per molecule.

Typical anionic cleansing surfactants for use in shampoo compositions of the invention include sodium oleyl succinate, ammonium lauryl sulphosuccinate, ammonium lauryl sulphate, sodium dodecylbenzene sulphonate, triethanolamine dodecylbenzene sulphonate, sodium cocoyl isethionate, sodium lauryl isethionate and sodium N-lauryl sarcosinate. The most preferred anionic surfactants are sodium lauryl sulphate, sodium lauryl ether sulphate(n)EO, (where n ranges from 1 to 3), ammonium lauryl sulphate and ammonium lauryl ether sulphate(n)EO, (where n ranges from 1 to 3).

Mixtures of any of the foregoing anionic cleansing surfactants may also be suitable.

The total amount of anionic cleansing surfactant in shampoo compositions of the invention is generally from 5 to 30, preferably from 6 to 20, more preferably from 8 to 16 wt %.

Co-surfactant

The shampoo composition can optionally include co-surfactants, to help impart aesthetic, physical or cleansing properties to the composition.

A preferred example is an amphoteric or zwitterionic surfactant, which can be included in an amount ranging from 0 to about 8, preferably from 1 to 4 wt %.

Examples of amphoteric and zwitterionic surfactants include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoos of the invention include lauryl amine oxide, cocodimethyl sulphopropyl betaine and preferably lauryl betaine, cocamidopropyl betaine and sodium cocamphopropionate.

Another preferred example is a nonionic surfactant, which can be included in an amount ranging from 0 to 8, preferably from 2 to 5 wt %.

For example, representative nonionic surfactants that can be included in shampoo compositions of the invention include condensation products of aliphatic ($C_8$–$C_{18}$) primary or secondary linear or branched chain alcohols or phenols with alkylene oxides, usually ethylene oxide and generally having from 6 to 30 ethylene oxide groups.

Other representative nonionic surfactants include mono- or di-alkyl alkanolamides. Examples include coco mono- or di-ethanolamide and coco mono-isopropanolamide.

Further nonionic surfactants which can be included in shampoo compositions of the invention are the alkyl polyglycosides (APGs). Typically, the APG is one which comprises an alkyl group connected (optionally via a bridging group) to a block of one or more glycosyl groups. Preferred APGs are defined by the following formula:

$$RO\text{---}(G)_n$$

wherein R is a branched or straight chain alkyl group which may be saturated or unsaturated and G is a saccharide group.

R may represent a mean alkyl chain length of from about $C_5$ to about $C_{20}$. Preferably R represents a mean alkyl chain length of from about $C_8$ to about $C_{12}$. Most preferably the value of R lies between about 9.5 and about 10.5. G may be selected from $C_5$ or $C_6$ monosaccharide residues, and is preferably a glucoside. G may be selected from the group comprising glucose, xylose, lactose, fructose, mannose and derivatives thereof. Preferably G is glucose.

The degree of polymerisation, n, may have a value of from about 1 to about 10 or more. Preferably, the value of n lies in the range of from about 1.1 to about 2. Most preferably the value of n lies in the range of from about 1.3 to about 1.5.

Suitable alkyl polyglycosides for use in the invention are commercially available and include for example those materials identified as: Oramix NS10 ex Seppic; Plantaren 1200 and Plantaren 2000 ex Henkel.

Other sugar-derived nonionic surfactants which can be included in shampoo compositions of the invention include the $C_{10}$–$C_{18}$ N-alkyl ($C_1$–$C_6$) polyhydroxy fatty acid amides, such as the $C_{12}$–$C_{18}$ N-methyl glucamides, as described for example in WO 92 06154 and U.S. Pat. No. 5,194,639, and the N-alkoxy polyhydroxy fatty acid amides, such as $C_{10}$–$C_{18}$ N-(3-methoxypropyl)glucamide.

The shampoo composition can also optionally include one or more cationic co-surfactants included in an amount ranging from 0.01 to 10, more preferably from 0.05 to 5, most preferably from 0.05 to 2 wt %. Useful cationic surfactants are described hereinbelow in relation to conditioner compositions.

The total amount of surfactant (including any co-surfactant, and/or any emulsifier) in shampoo compositions of the invention is generally from 5 to 50, preferably from 5 to 30, more preferably from 10 to 25 wt %.

Cationic Polymer

A cationic polymer is a preferred ingredient in shampoo compositions of the invention, for enhancing conditioning performance of the shampoo.

The cationic polymer may be a homopolymer or be formed from two or more types of monomers. The molecular weight of the polymer will generally be between 5000 and 10000000, typically at least 10000 and preferably in the range 100000 to about 2000000. The polymers will have cationic nitrogen containing groups such as quaternary ammonium or protonated amino groups, or a mixture thereof.

The cationic nitrogen-containing group will generally be present as a substituent on a fraction of the total monomer units of the cationic polymer. Thus when the polymer is not a homopolymer it can contain spacer non-cationic monomer units. Such polymers are described in the CTFA Cosmetic Ingredient Directory, 3rd edition. The ratio of the cationic to non-cationic monomer units is selected to give a polymer having a cationic charge density in the required range.

Suitable cationic conditioning polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1–C7 alkyl groups, more preferably C1–3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be polymerized in the amine form and then converted to ammonium by quaternization.

The cationic conditioning polymers can comprise mixtures of monomer units derived from amine- and/or quaternary ammonium-substituted monomer and/or compatible spacer monomers.

Suitable cationic conditioning polymers include, for example:

copolymers of 1-vinyl-2-pyrrolidine and 1-vinyl-3-methyl-imidazolium salt (e.g. chloride salt), referred to in the industry by the Cosmetic, Toiletry, and Fragrance Association, (CTFA) as Polyquaternium-16. This material is commercially available from BASF Wyandotte Corp. (Parsippany, N.J., USA) under the LUVIQUAT tradename (e.g. LUVIQUAT FC 370);

copolymers of 1-vinyl-2-pyrrolidine and dimethylaminoethyl methacrylate, referred to in the industry (CTFA) as Polyquaternium-11. This material is available commercially from Gaf Corporation (Wayne, N.J., USA) under the GAFQUAT tradename (e.g., GAFQUAT 755N);

cationic diallyl quaternary ammonium-containing polymers including, for example, dimethyldiallyammonium chloride homopolymer and copolymers of acrylamide and dimethyldiallylammonium chloride, referred to in the industry (CTFA) as Polyquaternium 6 and Polyquaternium 7, respectively;

mineral acid salts of amino-alkyl esters of homo-and co-polymers of unsaturated carboxylic acids having from 3 to 5 carbon atoms, (as described in U.S. Pat. No. 4,009,256);

cationic polyacrylamides(as described in WO95/22311).

Other cationic conditioning polymers that can be used include cationic polysaccharide polymers, such as cationic cellulose derivatives, cationic starch derivatives, and cationic guar gum derivatives. Suitably, such cationic polysaccharide polymers have a charge density in the range from 0.1 to 4 meq/g.

Cationic polysaccharide polymers suitable for use in compositions of the invention include those of the formula:

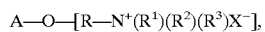

wherein: A is an anhydroglucose residual group, such as a starch or cellulose anhydroglucose residual. R is an alkylene, oxyalkylene, polyoxyalkylene, or hydroxyalkylene group, or combination thereof. $R^1$, $R^2$ and $R^3$ independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in $R^1$, $R^2$ and $R^3$) is preferably about 20 or less, and X is an anionic counterion.

Cationic cellulose is available from Amerchol Corp. (Edison, N.J., USA) in their Polymer JR and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

Other suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581).

A particularly suitable type of cationic polysaccharide polymer that can be used is a cationic guar gum derivative, such as guar hydroxypropyltrimonium chloride (commercially available from Rhone-Poulenc in their JAGUAR trademark series).

Examples are JAGUAR C13S, which has a low degree of substitution of the cationic groups and high viscosity. JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Preferably the cationic conditioning polymer is selected from cationic cellulose and cationic guar derivatives. Particularly preferred cationic polymers are JAGUAR C13S, JAGUAR C15, JAGUAR C17 and JAGUAR C16 and JAGUAR C162.

The cationic conditioning polymer will generally be present in compositions of the invention at levels of from 0.01 to 5, preferably from 0.05 to 1, more preferably from 0.08 to 0.5 wt %.

Conditioner Compositions

Compositions in accordance with the invention may also be formulated as conditioners for the treatment of hair (typically after shampooing) and subsequent rinsing.

Conditioning Surfactant

Such a conditioner will comprise one or more conditioning surfactants which are cosmetically acceptable and suitable for topical application to the hair.

Suitable conditioning surfactants are selected from cationic surfactants, used singly or in admixture.

Cationic surfactants useful in compositions of the invention contain amino or quaternary ammonium hydrophilic moieties which are positively charged when dissolved in the aqueous composition of the present invention.

Examples of suitable cationic surfactants are those corresponding to the general formula:

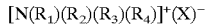

in which $R_1$, $R_2$, $R_3$, and $R_4$ are independently selected from (a) an aliphatic group of from 1 to 22 carbon atoms, or (b) an aromatic, alkoxy, polyoxyalkylene, alkylamido, hydroxyalkyl, aryl or alkylaryl group having up to 22 carbon atoms; and X is a salt-forming anion such as those selected from halogen, (e.g. chloride, bromide), acetate, citrate, lactate, glycolate, phosphate nitrate, sulphate, and alkylsulphate radicals.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated.

The most preferred cationic surfactants for conditioner compositions of the present invention are monoalkyl quaternary ammonium compounds in which the alkyl chain length is C8 to C14.

Suitable examples of such materials correspond to the general formula:

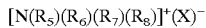

in which $R_5$ is a hydrocarbyl chain having 8 to 14 carbon atoms or a functionalised hydrocarbyl chain with 8 to 14 carbon atoms and containing ether, ester, amido or amino moieties present as substituents or as linkages in the radical chain, and $R_6$, $R_7$ and $R_8$ are independently selected from (a) hydrocarbyl chains of from 1 to about 4 carbon atoms, or (b) functionalised hydrocarbyl chains having from 1 to about 4 carbon atoms and containing one or more aromatic, ether, ester, amido or amino moieties present as substituents or as linkages in the radical chain, and X is a salt-forming anion such as those selected from halogen, (e.g. chloride, bromide), acetate, citrate, lactate, glycolate, phosphate nitrate, sulphate, and alkylsulphate radicals.

The functionalised hydrocarbyl chains (b) may suitably contain one or more hydrophilic moieties selected from alkoxy (preferably $C_1$–$C_3$ alkoxy), polyoxyalkylene (preferably $C_1$–$C_3$ polyoxyalkylene), alkylamido, hydroxyalkyl, alkylester, and combinations thereof.

Preferably the hydrocarbyl chains $R_1$ have 12 to 14 carbon atoms, most preferably 12 carbon atoms. They may be derived from source oils which contain substantial amounts of fatty acids having the desired hydrocarbyl chain length. For example, the fatty acids from palm kernel oil or coconut oil can be used as a source of C8 to C12 hydrocarbyl chains.

Typical monoalkyl quaternary ammonium compounds of the above general formula for use in shampoo compositions of the invention include:

(i) lauryl trimethylammonium chloride(available commercially as Arquad C35 ex-Akzo); cocodimethyl benzyl ammonium chloride (available commercially as Arquad DMCB-80 ex-Akzo)

(ii) compounds of the general formula:

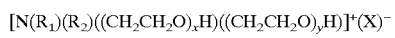

in which:

x+y is an integer from 2 to 20;

$R_1$ is a hydrocarbyl chain having 8 to 14, preferably 12 to 14, most preferably 12 carbon atoms or a functionalised hydrocarbyl chain with 8 to 14, preferably 12 to 14, most preferably 12 carbon atoms and containing ether, ester, amido or amino moieties present as substituents or as linkages in the radical chain;

$R_2$ is a $C_1$–$C_3$ alkyl group or benzyl group, preferably methyl, and

X is a salt-forming anion such as those selected from halogen, (e.g. chloride, bromide), acetate, citrate, lactate, glycolate, phosphate nitrate, sulphate, methosulphate and alkylsulphate radicals.

Suitable examples are PEG-n lauryl ammonium chlorides (where n is the PEG chain length), such as PEG-2 cocomonium chloride (available commercially as Ethoquad C12 ex-Akzo Nobel); PEG-2 cocobenzyl ammonium chloride (available commercially as Ethoquad CB/12 ex-Akzo Nobel); PEG-5 cocomonium methosulphate (available commercially as Rewoquat CPEM ex-Rewo); PEG-15 cocomonium chloride (available commercially as Ethoquad C/25 ex-Akzo)

(iii) compounds of the general formula:

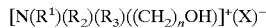

in which:

n is an integer from 1 to 4, preferably 2;

$R_1$ is a hydrocarbyl chain having 8 to 14, preferably 12 to 14, most preferably 12 carbon atoms;

$R_2$ and $R_3$ are independently selected from $C_1$–$C_3$ alkyl groups, and are preferably methyl, and X is a salt-forming anion such as those selected from halogen, (e.g. chloride, bromide), acetate, citrate, lactate, glycolate, phosphate nitrate, sulphate, and alkylsulphate radicals.

Suitable examples are lauryldimethylhydroxyethylammonium chloride (available commercially as Prapagen HY ex-Clariant)

Mixtures of any of the foregoing cationic surfactants compounds may also be suitable.

Examples of suitable cationic surfactants include:
quaternary ammonium chlorides, e.g. alkyltrimethylammonium chlorides wherein the alkyl group has from about 8 to 22 carbon atoms, for example octyltrimethylammonium chloride, dodecyltrimethylammonium chloride, hexadecyltrimethylammonium chloride, cetyltrimethylammonium chloride, octyldimethylbenzylammonium chloride, decyldimethylbenzylammonium chloride, stearyldi-methylbenzylammonium chloride, didodecyldimethylammonium chloride,
dioctadecyldimethylammonium chloride, tallow trimethylammonium chloride, cocotrimethylammonium chloride, and the corresponding salts thereof, e.g., bromides, hydroxides. Cetylpyridinium chloride or salts thereof, e.g., chloride
Quaternium-5
Quaternium-31
Quaternium-18
and mixtures thereof.

In the conditioners of the invention, the level of cationic surfactant is preferably from 0.01 to 10, more preferably 0.05 to 5, most preferably 0.1 to 2 wt % of the total composition.

Fatty Alcohol Material

Conditioner compositions of the invention preferably additionally comprise a fatty alcohol material. The combined use of fatty alcohol materials and cationic surfactants in conditioning compositions is believed to be especially advantageous, because this leads to the formation of a lamellar phase, in which the cationic surfactant is dispersed.

By "fatty alcohol material" is meant a fatty alcohol, an alkoxylated fatty alcohol, or a mixture thereof.

Representative fatty alcohols comprise from 8 to 22 carbon atoms, more preferably 16 to 20. Examples of suitable fatty alcohols include cetyl alcohol, stearyl alcohol and mixtures thereof. The use of these materials is also advantageous in that they contribute to the overall conditioning properties of compositions of the invention.

Alkoxylated, (e.g. ethoxylated or propoxylated) fatty alcohols having from about 12 to about 18 carbon atoms in the alkyl chain can be used in place of, or in addition to, the fatty alcohols themselves. Suitable examples include ethylene glycol cetyl ether, polyoxyethylene (2) stearyl ether, polyoxyethylene (4) cetyl ether, and mixtures thereof.

The level of fatty alcohol material in conditioners of the invention is suitably from 0.01 to 15, preferably from 0.1 to 10, and more preferably from 0.1 to 5 wt %. The weight ratio of cationic surfactant to fatty alcohol is suitably from 10:1 to 1:10, preferably from 4:1 to 1:8, optimally from 1:1 to 1:7, for example 1:3.

Conditioner compositions of the invention can also contain a cationic polymer. Suitable cationic polymers are described hereinabove in relation to shampoo compositions.

Optional Ingredients
Suspending Agents

In a preferred embodiment, the hair care composition, especially if it is a shampoo composition, further comprises from 0.1 to 5 wt % of a suspending agent for the coated particles. Suitable suspending agents are selected from polyacrylic acids, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearate, alkanolamides of fatty acids having from 16 to 22 carbon atoms and mixtures thereof. Ethylene glycol distearate and polyethylene glycol 3 distearate are preferred long chain acyl derivatives. Polyacrylic acid is available commercially as Carbopol 420, Carbopol 488 or Carbopol 493. Polymers of acrylic acid cross-linked with a polyfunctional agent may also be used, they are available commercially as Carbopol 910, Carbopol 934, Carbopol 940, Carbopol 941 and Carbopol 980. An example of a suitable copolymer of a carboxylic acid containing a monomer and acrylic acid esters is Carbopol 1342. All Carbopol (trademark) materials are available from Goodrich.

Suitable cross-linked polymers of acrylic acid and acrylate esters are Pemulen TR1 or Pemulen TR2. A suitable heteropolysaccharide gum is xanthan gum, for example that available as Kelzan mu.

The suspending agent for the coated particles is preferably a polymeric suspending agent.

Conditioning Agents

The compositions of this invention can also contain one or more conditioning agents selected from silicone conditioning agents and non-silicone oily conditioning agents.

When conditioning agent is present in the hair care compositions in droplet form, the droplets may be liquid, semi-solid or solid in nature, so long as they are substantially uniformly dispersed in the fully formulated product. Any droplets of oily conditioning agent are preferably present as either liquid or semi-solid droplets, more preferably as liquid droplets.

Silicone Conditioning Agents

The compositions of the invention can contain, emulsified droplets of a silicone conditioning agent, for enhancing conditioning performance. The silicone is insoluble in the aqueous matrix of the composition and so is present in an emulsified form, with the silicone present as dispersed droplets.

Suitable silicones include polydiorganosiloxanes, in particular polydimethylsiloxanes which have the CTFA designation dimethicone. Also suitable for use compositions of the invention (particularly shampoos and conditioners) are polydimethyl siloxanes having hydroxyl end groups, which have the CTFA designation dimethiconol. Also suitable for use in compositions of the invention are silicone gums having a slight degree of cross-linking, as are described for example in WO 96/31188. These materials can impart body, volume and stylability to hair, as well as good wet and dry conditioning.

The viscosity of the emulsified silicone itself (not the emulsion or the final hair conditioning composition) is typically at least 10,000 cst. In general we have found that conditioning performance increases with increased viscosity. Accordingly, the viscosity of the silicone itself is preferably at least 60,000 cst, most preferably at least 500,000 cst, ideally at least 1,000,000 cst. Preferably the viscosity does not exceed $10^9$ cst for ease of formulation.

Emulsified silicones for use in the shampoo compositions of the invention will typically have an average silicone droplet size in the composition of less than 30, preferably less than 20, more preferably less than 10 $\mu$m. We have found that reducing the droplet size generally improves conditioning performance. Most preferably the average silicone droplet size of the emulsified silicone in the composition is less than 2 $\mu$m, ideally it ranges from 0.01 to 1 $\mu$m. Silicone emulsions having an average silicone droplet size of $\leq 0.15$ $\mu$m are generally termed microemulsions.

Suitable silicone emulsions for use in the invention are also commercially available in a pre-emulsified form.

Examples of suitable pre-formed emulsions include emulsions DC2-1766, DC2-1784, and microemulsions DC2-1865 and DC2-1870, all available from Dow Corning. These are all emulsions/microemulsions of dimethiconol. Cross-linked silicone gums are also available in a pre-emulsified form, which is advantageous for ease of formulation. A preferred example is the material available from Dow Corning as DC X2-1787, which is an emulsion of cross-linked dimethiconol gum. A further preferred example is the material available from Dow Corning as DC X2-1391, which is a microemulsion of cross-linked dimethiconol gum.

A further preferred class of silicones for inclusion in shampoos and conditioners of the invention are amino functional silicones. By "amino functional silicone" is meant a silicone containing at least one primary, secondary or tertiary amine group, or a quaternary ammonium group.

Examples of suitable amino functional silicones include:
(i) polysiloxanes having the CTFA designation "amodimethicone", and the general formula:

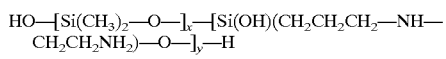

in which x and y are numbers depending on the molecular weight of the polymer, generally such that the molecular weight is between about 5,000 and 500,000.

(ii) polysiloxanes having the general formula:

in which:
G is selected from H, phenyl, OH or $C_{1-8}$ alkyl, e.g. methyl;
a is 0 or an integer from 1 to 3, preferably 0;
b is 0 or 1, preferably 1;
m and n are numbers such that (m+n) can range from 1 to 2000, preferably from 50 to 150;
m is a number from 1 to 2000, preferably from 1 to 10;
n is a number from 0 to 1999, preferably from 49 to 149, and
R' is a monovalent radical of formula $—C_qH_{2q}L$ in which q is a number from 2 to 8 and L is an aminofuctional group selected from the following:
—NR"—CH$_2$—CH$_2$—N(R")$_2$
—N(R")$_2$
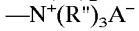
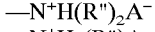
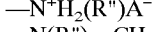
—N(R")—CH$_2$—CH$_2$—N$^+$H$_2$(R")A$^-$
in which R" is selected from H, phenyl, benzyl, or a saturated monovalent hydrocarbon radical, e.g. $C_{1-20}$ alkyl, and A is a halide ion, e.g. chloride or bromide.

Suitable amino functional silicones corresponding to the above formula include those polysiloxanes termed "trimethylsilylamodimethicone" as depicted below, and which are sufficiently water insoluble so as to be useful in compositions of the invention:

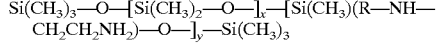

wherein x+y is a number from about 50 to about 500, and wherein R is an alkylene group having from 2 to 5 carbon atoms. Preferably, the number x+y is in the range of from about 100 to about 300.

(iii) quaternary silicone polymers having the general formula:

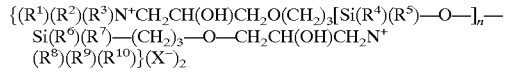

wherein $R^1$ and $R^{10}$ may be the same or different and may be independently selected from H, saturated or unsaturated long or short chain alk(en)yl, branched chain alk(en)yl and $C_5$–$C_8$ cyclic ring systems;

$R^2$ thru $R^9$ may be the same or different and may be independently selected from H, straight or branched chain lower alk(en)yl, and $C_5$–$C_8$ cyclic ring systems;

n is a number within the range of about 60 to about 120, preferably about 80, and X$^-$ is preferably acetate, but may instead be for example halide, organic carboxylate, organic sulphonate or the like. Suitable quaternary silicone polymers of this class are described in EP-A-0 530 974.

Amino functional silicones suitable for use in shampoos and conditioners of the invention will typically have a mole % amine functionality in the range of from about 0.1 to about 8.0 mole %, preferably from about 0.1 to about 5.0 mole %, most preferably from about 0.1 to about 2.0 mole %. In general the amine concentration should not exceed about 8.0 mole % since we have found that too high an amine concentration can be detrimental to total silicone deposition and therefore conditioning performance.

The viscosity of the amino functional silicone is not particularly critical and can suitably range from about 100 to about 500,000 cst.

Specific examples of amino functional silicones suitable for use in the invention are the aminosilicone oils DC2-8220, DC2-8166, DC2-8466, and DC2-8950-114 (all ex Dow Corning), and GE 1149-75, (ex General Electric Silicones).

Also suitable are emulsions of amino functional silicone oils with non ionic and/or cationic surfactant.

Suitably such pre-formed emulsions will have an average amino functional silicone droplet size in the shampoo composition of less than 30, preferably less than 20, more preferably less than 10 μm. Again, we have found that reducing the droplet size generally improves conditioning performance. Most preferably the average amino functional silicone droplet size in the composition is less than 2 μm ideally it ranges from 0.01 to 1 μm.

Pre-formed emulsions of amino functional silicone are also available from suppliers of silicone oils such as Dow Corning and General Electric. Specific examples include DC929 Cationic Emulsion, DC939 Cationic Emulsion, and the non-ionic emulsions DC2-7224, DC2-8467, DC2-8177 and DC2-8154 (all ex Dow Corning).

An example of a quaternary silicone polymer useful in the present invention is the material K3474, ex Goldschmidt.

For shampoo compositions according to the invention intended for the treatment of "mixed" hair (i.e. greasy roots and dry ends), it is particularly preferred to use a combination of amino functional and non-amino functional silicone in compositions of the invention, especially when these are in the form of shampoo compositions. In such a case, the weight ratio of amino functional silicone to non-amino functional silicone will typically range from 1:2 to 1:20, preferably 1:3 to 1:20, more preferably 1:3 to 1:8.

The total amount of silicone incorporated into compositions of the invention depends on the level of conditioning desired and the material used. A preferred amount is from 0.01 to 10 wt % although these limits are not absolute. The lower limit is determined by the minimum level to achieve conditioning and the upper limit by the maximum level to avoid making the hair and/or skin unacceptably greasy.

We have found that a total amount of silicone of from 0.3 to 5, preferably 0.5 to 3 wt % is a suitable level.

The viscosity of silicones and silicone emulsions can be measured by means of a glass capillary viscometer as set out further in Dow Corning Corporate Test Method CTM004, Jul. 20, 1970.

In compositions comprising silicone, it is preferred that a suspending agent for the silicone also be present. Suitable suspending agents are as described hereinabove.

(ii) Non-silicone Oily Conditioning Components

Compositions according to the present invention may also comprise a dispersed, non-volatile, water-insoluble oily conditioning agent.

This component will be dispersed in the composition in the form of droplets, which form a separate, discontinuous phase from the aqueous, continuous phase of the composition. In other words, the oily conditioning agent will be present in the shampoo composition in the form of an oil-in-water emulsion.

By "insoluble" is meant that the material is not soluble in water (distilled or equivalent) at a concentration of 0.1% (w/w), at 250° C.

Suitably, the $D_{3,2}$ average droplet size of the oily conditioning component is at least 0.4, preferably at least 0.8, and more preferably at least 1 µm. Additionally, the $D_{3,2}$ average droplet size of the oily conditioning component is preferably no greater than 10, more preferably no greater 8, more preferably no greater than 5, yet more preferably no greater than 4, and most preferably no greater than 3.5 µm.

The oily conditioning agent may suitably be selected from oily or fatty materials, and mixtures thereof.

Oily or fatty materials are preferred conditioning agents in the shampoo compositions of the invention for adding shine to the hair and also enhancing dry combing and dry hair feel.

Preferred oily and fatty materials will generally have a viscosity of less than 5 Pa.s, more preferably less than 1 Pa.s, and most preferably less than 0.5 Pa.s, e.g. 0.1 Pa.s and under as measured at 25° C. with a Brookfield Viscometer (e.g. Brookfield RV) using spindle 3 operating at 100 rpm.

Oily and fatty materials with higher viscosities may be used. For example, materials with viscosities as high as 65 Pa.s may be used. The viscosity of such materials (i.e. materials with viscosities of 5 Pa.s and greater) can be measured by means of a glass capillary viscometer as set out further in Dow Corning Corporate Test Method CTM004, Jul. 20, 1970.

Suitable oily or fatty materials are selected from hydrocarbon oils, fatty esters and mixtures thereof.

Hydrocarbon oils include cyclic hydrocarbons, straight chain aliphatic hydrocarbons (saturated or unsaturated), and branched chain aliphatic hydrocarbons (saturated or unsaturated). Straight chain hydrocarbon oils will preferably contain from about 12 to about 30 carbon atoms. Branched chain hydrocarbon oils can and typically may contain higher numbers of carbon atoms. Also suitable are polymeric hydrocarbons of alkenyl monomers, such as $C_2$–$C_6$ alkenyl monomers. These polymers can be straight or branched chain polymers. The straight chain polymers will typically be relatively short in length, having a total number of carbon atoms as described above for straight chain hydrocarbons in general. The branched chain polymers can have substantially higher chain length. The number average molecular weight of such materials can vary widely, but will typically be up to about 2000, preferably from about 200 to about 1000, more preferably from about 300 to about 600. Specific examples of suitable hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used. Exemplary branched-chain isomers are highly branched saturated or unsaturated alkanes, such as the permethyl-substituted isomers e.g., the permethyl-substituted isomers of hexadecane and eicosane, such as 2, 2, 4, 4, 6, 6, 8, 8-dimethyl-10-methylundecane and 2, 2, 4, 4, 6, 6-dimethyl-8-methylnonane, sold by Permethyl Corporation. A further example of a hydrocarbon polymer is polybutene, such as the copolymer of isobutylene and butene. A commercially available material of this type is L-14 polybutene from Amoco Chemical Co. (Chicago, Ill., U.S.A.).

Particularly preferred hydrocarbon oils are the various grades of mineral oils. Mineral oils are clear oily liquids obtained from petroleum oil, from which waxes have been removed, and the more volatile fractions removed by distillation. The fraction distilling between 250° C. to 300° C. is termed mineral oil, and it consists of a mixture of hydrocarbons ranging from $C_{16}H_{34}$ to $C_{21}H_{44}$. Suitable commercially available materials of this type include Sirius M85 and Sirius M125, all available from Silkolene.

Suitable fatty esters are characterised by having at least 10 carbon atoms, and include esters with hydrocarbyl chains derived from fatty acids or alcohols, e.g., monocarboxylic acid esters, polyhydric alcohol esters, and di- and tricarboxylic acid esters. The hydrocarbyl radicals of the fatty esters hereof can also include or have covalently bonded thereto other compatible functionalities, such as amides and alkoxy moieties, such as ethoxy or ether linkages.

Monocarboxylic acid esters include esters of alcohols and/or acids of the formula R'COOR in which R' and R independently denote alkyl or alkenyl radicals and the sum of carbon atoms in R' and R is at least 10, preferably at least 20.

Specific examples include, for example, alkyl and alkenyl esters of fatty acids having aliphatic chains with from about 10 to about 22 carbon atoms, and alkyl and/or alkenyl fatty alcohol carboxylic acid esters having an alkyl and/or alkenyl alcohol-derived aliphatic chain with about 10 to about 22 carbon atoms, benzoate esters of fatty alcohols having from about 12 to 20 carbon atoms.

The monocarboxylic acid ester need not necessarily contain at least one chain with at least 10 carbon atoms, so long as the total number of aliphatic chain carbon atoms is at least 10. Examples include isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

Di- and trialkyl and alkenyl esters of carboxylic acids can also be used. These include, for example, esters of $C_4$–$C_8$ dicarboxylic acids such as $C_1$–$C_{22}$ esters (preferably $C_1$–$C_6$) of succinic acid, glutaric acid, adipic acid, hexanoic acid, heptanoic acid, and octanoic acid. Examples include diisopropyl adipate, diisohexyl adipate, and diisopropyl sebacate. Other specific examples include isocetyl stearoyl stearate, and tristearyl citrate.

Polyhydric alcohol esters include alkylene glycol esters, for example ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol monostearate, ethoxylated propylene glycol monostearate, polyglycerol polyfatty acid esters, ethoxylated glyceryl monostearate, 1,3-butylene glycol monostearate, 1,3-butylene glycol distearate, polyoxyethylene polyol fatty acid ester, sorbitan fatty acid esters, polyoxyethylene sorbitan fatty acid esters and mono-, di-and triglycerides.

Particularly preferred fatty esters are mono-, di- and triglycerides, more specifically the mono-, di-, and triesters of glycerol and long chain carboxylic acids such as $C_1$–$C_{22}$ carboxylic acids. A variety of these types of materials can be obtained from vegetable and animal fats and oils, such as coconut oil, castor oil, safflower oil, sunflower oil, cottonseed oil, corn oil, olive oil, cod liver oil, almond oil, avocado oil, palm oil, sesame oil, peanut oil, lanolin and soybean oil. Synthetic oils include triolein and tristearin glyceryl dilaurate.

Specific examples of preferred materials include cocoa butter, palm stearin, sunflower oil, soyabean oil and coconut oil.

The oily or fatty material is suitably present at a level of from 0.05 to 10, preferably from 0.2 to 5, more preferably from about 0.5 to 3 wt %.

The compositions of this invention preferably contain no more than 3 wt % of a styling polymer, more preferably less than 1% of a styling polymer, preferably contain less than 0.1% by weight a styling polymer, and optimally are free of styling polymer.

In hair care compositions containing a conditioning agent, it is preferred that a cationic polymer also be present.

Adjuvants

The compositions of the present invention may also contain adjuvants suitable for hair care. Generally such ingredients are included individually at a level of up to 2, preferably up to 1 wt % of the total composition.

Among suitable hair care adjuvants, are:

(i) natural hair root nutrients, such as amino acids and sugars. Examples of suitable amino acids include arginine, cysteine, glutamine, glutamic acid, isoleucine, leucine, methionine, serine and valine, and/or precursors and derivatives thereof. The amino acids may be added singly, in mixtures, or in the form of peptides, e.g. di- and tripeptides. The amino acids may also be added in the form of a protein hydrolysate, such as a keratin or collagen hydrolysate. Suitable sugars are glucose, dextrose and fructose. These may be added singly or in the form of, e.g. fruit extracts. A particularly preferred combination of natural hair root nutrients for inclusion in compositions of the invention is isoleucine and glucose. A particularly preferred amino acid nutrient is arginine.

(ii) hair fibre benefit agents. Examples are:
ceramides, for moisturising the fibre and maintaining cuticle integrity. Ceramides are available by extraction from natural sources, or as synthetic ceramides and pseudoceramides. A preferred ceramide is Ceramide II, ex Quest. Mixtures of ceramides may also be suitable, such as Ceramides LS, ex Laboratoires Serobiologiques.

The invention will now be further illustrated by the following, non-limiting Examples.

EXAMPLES

Procedure for the Delamination Process of the Clay

The clay materials were dispersed in water and high sheared at room temperature for 15 minutes by using a Silverson mixer.

Functionalising Clays

Clays were functionalised according to the procedures stated in R. Dagani, Chemical and Engineering News, June; 1999; 25; A. P. Jackson, J. F. V. Vincent. J. Mater.Sci., 25 (1990)3173 and E. P. Giannelis, Adv.Mater., 8(1996)29.

Assessment

Bentonite type clay materials were functionalised with C8, C10 and C18 carboxy functional groups and assessed in a half head mannequin test. The clays were de-laminated. The mannequin hair was washed twice with 3 g of a conventional shampoo and treated with 3 g of an off the shelf rinse-off conditioner once. The hair was divided in two and 5 ml of an aqueous dispersion of the functionalised clay particles (at a level of about 500 ppm) applied all over half the hair. This was left on. The hair was allowed to dry and the two halves of the hair were assessed by a trained analyst.

For all three functionalised clays, the half head treated with the coated particles demonstrated a higher root lift than the half head which had not been treated.

The above procedure was repeated using bentone functionalised with a trimethyl siloxy group, (HMDXZ), 2-aminoethyl-3-aminopropyl, aminopropyl or octadecylammonium groups. The clays were de-laminated and the testing procedure stated above repeated.

| Example | Root Lift | Visual Volume |
| --- | --- | --- |
| Un-functionalised Bentone | 1 | 2 |
| Functionalised with HMDZ | 3 | 3 |
| Functionalised with 2-amino ethyl-3-aminopropyl | 4 | 4 |
| Functionalised with Aminopropyl | 4 | 4 |
| Functionalised with Octadecylammonium | 2 | 4 |

Conditioning compositions was made having the following formulation:

| | Conditoner Compositions | | | |
| --- | --- | --- | --- | --- |
| | Wt % | | | |
| | Example 1 | Example 2 | Example 3 | Example 4 |
| Citric acid 50% active | 0.015 | 0.015 | 0.015 | 0.015 |
| PEG-2 oleamonium chloride & propylene glycol | 2.0 | 2.0 | 2.0 | 2.0 |
| Cetyl/stearyl alcohol | 8.0 | 8.0 | 8.0 | 8.0 |
| Disodium EDTA | 0.1 | 0.1 | 0.1 | 0.1 |
| DMDM hydantoin 55% active | 0.1 | 0.1 | 0.1 | 0.1 |
| Silicone DC245 | 1.8 | 1.5 | 1.5 | 1.5 |
| HMDZ bentonite | 1.0 | 0.5 | 0.7 | 0.2 |
| Fragrance | 0.6 | 0.6 | 0.6 | 0.6 |
| Water and minors | To 100 wt % | | | |
| Root lift | 2 | 2 | 3 | 2 |
| Visual volume | 2 | 2 | 3 | 2 |

What is claimed is:

1. A method of treating hair comprising:
i) wetting the hair;
ii) applying an aqueous hair care composition comprising water-insoluble particles having a layered structure which is a clay in which organic functional groups have been introduced during formation of the clay, the organic functional groups being covalently bonded to silicone in the clay, and wherein the particles have the formula:

$$Mg_6Si_8R_8O_{16}(OH)_4,$$

wherein R is an organic functional group selected from $C_1$–$C_{20}$ alkyl, alkenyl, alkynyl, aralkyl and aryl groups, optionally substituted with one or more of the same or different groups selected from halo, OR', $OCOR^1$, $NR^2R^3$, $N^+R^4R^5R^6$, COX, NCO, $NO_2$, $SO_2R^7$, $SO_3H$, $H_2PO_4$, $PO(OR')_2$ and heterocycloalkyl, wherein X is selected from halo, $OR^8$, $OCOR^9$, OH, H and $R^{10}$ and R', $R^1$, $R^2$, $R^3$, $R^4$, $R^5$, $R^6$, $R^7$, $R^8$, $R^9$ and $R^{10}$ are independently selected from $C_1$ to $C_6$ alkyl, $C_2$ to $C_6$ alkenyl and hydrogen, and when organic functional groups comprise $CO_2H$, $SO_3H$, OH or $H_2PO_4$, they may be in salt form;

iii) rinsing the hair.

2. A method according to claim 1 in which the optional substituent is a quaternary ammonium group.

3. A method according to claim 1 in which the smallest dimension of the water in-soluble particle is no more than 10% of the biggest dimension of the particle.

4. A method according to claim 1, in which the water insoluble particles are present in an amount of from 0.01 to 10 wt %.

5. A method according to claim 1, which is a shampoo composition comprising at least one cleansing surfactant selected from anionic, amphoteric and zwitterionic surfactants and mixtures thereof, and further comprising a cationic polymer.

6. A method according to claim 1, which is a conditioner composition comprising at least one conditioning surfactant and a fatty alcohol material.

7. A method according to claim 1 in which the clay is trimethyl siloxyl bentonite.

* * * * *